United States Patent [19]
DeLuca et al.

[11] 4,336,193
[45] Jun. 22, 1982

[54] PROCESS FOR PREPARING VITAMIN D-LACTONES

[75] Inventors: Hector F. DeLuca; Heinrich K. Schnoes, both of Madison; Herbert E. Paaren, Verona; Joseph K. Wichmann; Mary A. Fivizzani, both of Madison, all of Wis.

[73] Assignee: Wisconsin Alumni Research Foundation, Madison, Wis.

[21] Appl. No.: 228,486

[22] Filed: Jan. 26, 1981

Related U.S. Application Data

[63] Continuation-in-part of Ser. No. 174,944, Aug. 4, 1980, abandoned.

[51] Int. Cl.$^3$ ............................ C07J 9/00; C07J 17/00
[52] U.S. Cl. ............................. 260/239.57; 260/397.1; 260/397.2
[58] Field of Search .............. 260/239.57, 397.1, 397.2

[56] References Cited

U.S. PATENT DOCUMENTS 3,547,911 12/1970 Fried et al. ...................... 260/239.57
4,134,904 1/1979 Kaiser .............................. 260/397.2
4,183,852 1/1980 Kaiser .............................. 260/397.2

Primary Examiner—Elbert L. Roberts
Attorney, Agent, or Firm—Howard W. Bremer

[57] ABSTRACT

The invention provides methods for preparing the various isomeric forms of 25-hydroxyvitamin $D_3$-26,23-lactone utilizing cyanohydrin formation with readily prepared steroid materials followed by actinic radiation of the products and recovery of the desired 25-hydroxyvitamin $D_3$-26,23-lactone.

The invention also provides new intermediate compounds in their various isomeric forms derived during the process for preparing the said vitamin $D_3$ lactones.

25-Hydroxyvitamin $D_3$-26,23-lactone is recognized as having vitamin D-like activity and is believed to play an important role in the regulation of calcium and phosphate levels in the animal and human organism. The present invention provides a convenient method for preparing the various isomeric forms of this compound.

16 Claims, No Drawings

PROCESS FOR PREPARING VITAMIN D-LACTONES

The invention described herein was made in the course of work under a grant or award from the Department of Health and Human Services.

This application is a continuation-in-part of Ser. No. 174,944, filed Aug. 4, 1980, now abandoned.

DESCRIPTION

1. Technical Field

This invention relates to the preparation of biologically active vitamin D derivatives.

More specifically this invention relates to a process for the preparation of 25-hydroxyvitamin $D_3$-26,23-lactone and to novel compounds which are synthetic intermediates in this process.

It is now well-established that the biological function of vitamin D in the animal or human is dependent on metabolism of the vitamin to hydroxylated forms. A number of metabolites have been identified, e.g. 25-hydroxyvitamin $D_3$, 24,25-dihydroxyvitamin $D_3$, 1,25-dihydroxyvitamin $D_3$, and it is now generally accepted that one or more of these metabolites are the compounds responsible for the biological action associated with vitamin D, namely the control of calcium and phosphorus homeostasis in the animal or human.

2. Background Art

Because of their biological potency, vitamin D metabolites are of great therapeutic interest, and their preparation, efficacy and use is amply documented in the patent and other literature, e.g. U.S. Pat. Nos. 3,880,894 (1,25-dihydroxyergocalciferol); 3,879,548 (method of treating milk fever in dairy cattle with 1α-hydroxycholecalciferol); 3,715,374 (24,25-dihydroxycholecalciferol); 3,697,559 (1,25-dihydroxycholecalciferol). In addition, various structural analogs of these compounds are of scientific and commercial interest as substitutes for the natural metabolites in various clinical application, e.g. U.S. Pat. Nos. 4,201,881 (24,24-difluoro-1α,25-dihydroxycholecalciferol); 4,196,133 (24,24-difluoro-25-hydroxycholecalciferol); 3,786,062 (22-dehydro-25-hydroxycholecalciferol).

More recently a novel vitamin $D_3$ metabolite, characterized by an unusual lactone unit in the steroid side chain was discovered (Wichmann et al. *Biochemistry* 18, 4775–4780, 1979). The compound, 25-hydroxyvitamin $D_3$-26,23-lactone, may be represented by the structure shown below,

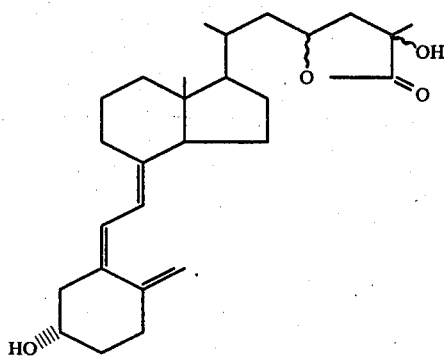

The 25-hydroxy-vitamin $D_3$-lactone, exhibits vitamin D-like activity and is believed to play an important role in the control of calcium and phosphate levels in the animal organism.

DISCLOSURE OF INVENTION

The present invention provides a process for preparing 25-hydroxyvitamin $D_3$-26,23-lactone from readily available steroid starting materials as is more fully described in the following specification and as claimed in the appended claims.

In this Description and in the claims the word "acyl" means an aliphatic acyl group of from 1 to about 5 carbon atoms, such as acetyl, propionyl, butyryl, pentoyl and their isomeric forms, or an aromatic acyl group, such as benzoyl, or substituted benzoyl, e.g. methyl benzoyl, nitrobenzoyl or halobenzoyl. The term "alkyl" denotes a hydrocarbon radical of from 1 to about 5 carbon atoms such as methyl, ethyl, propyl, etc., or their corresponding isomeric forms.

BEST MODE FOR CARRYING OUT THE INVENTION

As depicted in Process Schematic 1, the present process utilizes the 5,7-diene ester (1) as the starting material, where $R_1$ is hydrogen or a hydroxy protecting group such as acyl, alkylsilyl, or tetrahydropyranyl and where R' is hydrogen or an alkyl group of from 1–5 carbons. This 5,7-diene ester is readily obtained from the known 24-nor-5-cholenic acid or its esters employing well known processes for introducing the 7,8-double bond.

PROCESS SCHEMATIC I

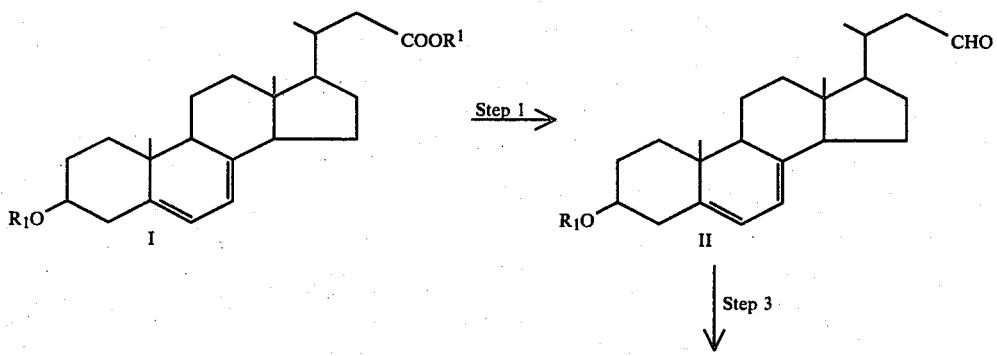

-continued
PROCESS SCHEMATIC I

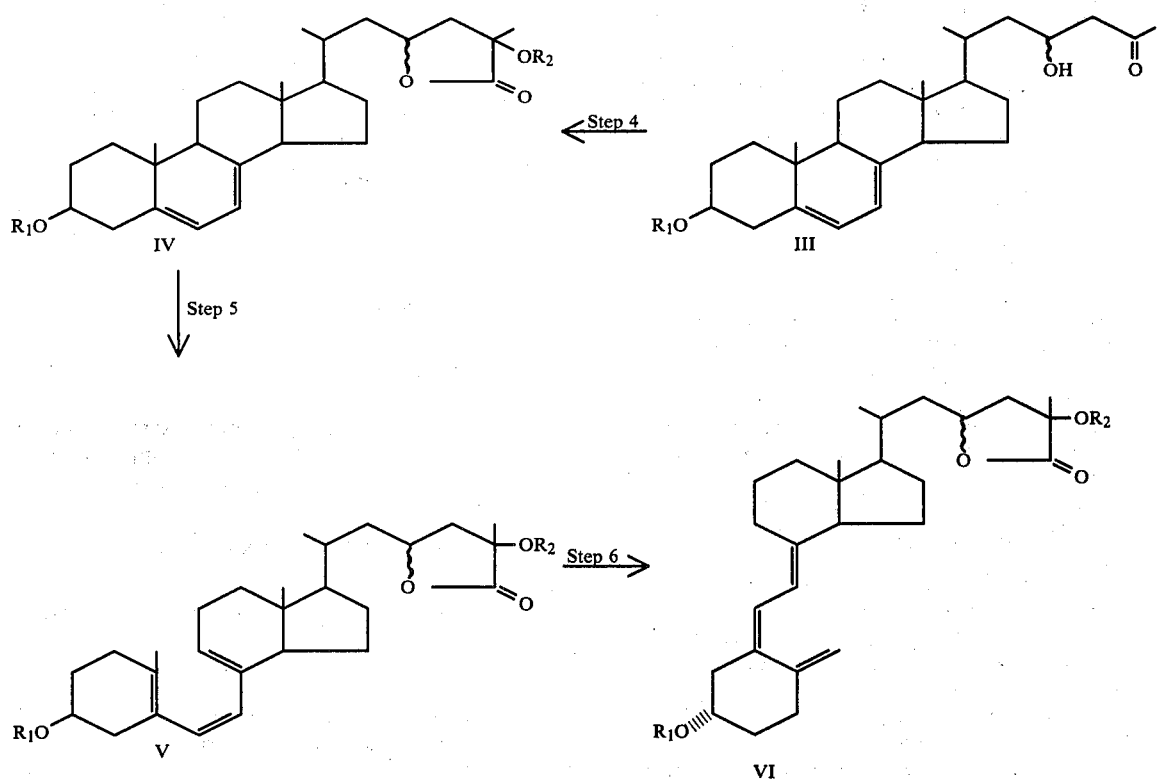

In accordance with the process shown in Process Schematic 1 the 23-acid or ester function in 1 is subjected to a hydride reduction to form the corresponding aldehyde represented by structure 11. This reduction is conducted in a suitable solvent (e.g. ether, THF, benzene, etc.) at moderate or low temperatures with sterically bulky aluminum hydrides, such as di-t-butyl aluminum hydrides as preferred reagents since, with such reagents, the reaction may be stopped at the aldehyde stage. If the hydroxy protecting group $R_1$ in compound 1 is an acyl group, such a group would, of course, be removed in the hydride reduction step to yield aldehyde 11, where $R_1=H$. Reprotection is not necessary, but if desired, can be accomplished readily by well-known procedures (e.g. acylation, alkylsilylation, tetrahydropyranylation) to yield aldehyde 11, where $R_1=$acyl, alkylsilyl or THP. Alternatively, and especially in those cases where the protecting group $R_1$ in compound 1 is a group stable to hydride reagents (e.g. tetrahydropyranyl (THP) or alkylsilyl group) the conversion of 1 to aldehyde 11 can be conducted as a two-step process, involving first the reduction of the acid or ester function to alcohol and then reoxidation of the 23-alcohol to the aldehyde. Such processes are well known in the art.

The resulting aldehyde 11 (where $R_1$ is hydrogen or a hydroxy-protecting group) is then subjected to an aldol condensation reaction (step 2 in Process Schematic 1) with acetone, or the synthetic equivalent of the acetone reagent, e.g. the derived imine such as acetonecyclohexylimine, in the presence of a catalyst and suitable solvent (e.g. acetone, ether, etc.). With acetone as the reagent, a basic catalyst is preferred, such as a solution of potassium hydroxide or similar base. Organic bases may also be used, e.g. $NaOCH_3$, or potassium-t-butoxide, lithium isopropylamide, etc. The product of this aldol condensation reaction in the hydroxy ketone, represented as structure 111 in Process Schematic 1, where $R_1$ is hydrogen or a hydroxy protecting group as previously defined. This hydroxy-ketone product is a mixture of two stereoisomers, differing in C-23-hydroxy-configuration in accordance with the following structural formulas.

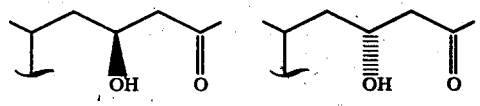

This mixture can be separated by any of the well known isomer separation methods, e.g. crystallization, or, preferably chromatography on either thin layer plates or efficient columns, e.g. by high-performance liquid chromatography (HPLC) and the two C-23-hydroxy epimers can then be subjected separately to the subsequent steps of the process.

Alternatively the hydroxy-ketone product (111) can be subjected directly to the next step of the process (step 3 in Process Schematic 1) which involves, lactone formation in the side chain. The transformation is accomplished by treating hydroxy-ketone 111 with cyanide (e.g. KCN) in the presence of base (e.g. hydroxide) and a suitable solvent, e.g. alcohol or alcohol/water mixtures, to obtain the intermediate cyanohydrin at carbon 25, which is not isolated but directly converted under these conditions to the hydroxy-acid and then lactonized in acid (e.g. HCl) to form the desired lactone product represented by the structure IV in Process Schematic 1. C-3-Hydroxy-protecting groups that may be present in the hydroxy-ketone 111 subjected to lactone formation will usually be removed during this lactonization process involving both base and acid treatment and the lactone product obtained can normally be represented by structure IV, where $R_1=H$, $R_2=H$. Reprotection of the hydroxy group is not necessary, but can, if desired, be accomplished by any of the known methods of acylation, alkylsilylation, etc. to obtain lactone derivatives of structure IV where $R_1$ or $R_2$ or both are hydroxy-protecting groups, such as acyl, alkylsilyl, etc.

Cyanohydrin formation can also be accomplished by a cyanohydrin exchange reaction involving, for example, treatment of hydroxy ketone 111 with acetone cyanohydrin in the presence of a suitable catalyst, e.g. KOH, $NaOCH_3$, potassium t-butoxide. Since formation of the cyanohydrin results in generation of another asymmetric center at C-25, lactone IV, as prepared from the hydroxy-ketone 111 (representing two C-23-hydroxy stereo-isomers, supra), now consists of a mixture of four stereo-isomeric products differing in steric configuration at C-23 and C-25 as represented by the following structural formulas.

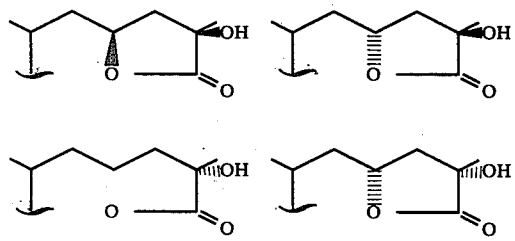

The stereoisomeric mixture of lactone IV may be separated at this stage, preferable by high-performance liquid chromatography (HPLC), to obtain the four stereo isomeric forms, designated here for convenience as IVA, IVB, IVC and IVD, in the order of their elution from HPLC, in pure form. Each of the lactone stereo-isomers is then subjected to photoylsis under ultraviolet irradiation (step 4 in Process Schematic 1) in a suitable solvent (e.g. ether, alcohol, benzene, or mixtures of ether and other solvents, e.g. benzene) to obtain the corresponding previtamin D lactone derivatives represented by general structure V (where $R_1=R_2=H$, or a hydroxy-protecting group).

Subsequent isomerization of each of the previtamin lactone isomers depicted by general structure V to the corresponding vitamin lactone, represented by general structure VI (where $R_1=R_2=H$ or where any or both of $R_1$ and $R_2$ may represent a hydroxy-protecting group) (step 5 in Process Schematic 1) is accomplished by heating the previtamin intermediates to moderate temperature (e.g. 50°-80° C.) in a suitable solvent, e.g. on low molecular weight alcohol, or benzene, or toluene. This two-step irradiation/thermal isomerization sequence yields from lactone isomer IVA the corresponding vitamin lactone VIA, from isomer IVB, the vitamin lactone VIB, from isomer IVC the corresponding vitamin lactone VIC, and from isomer IVD the vitamin lactone VID, all in pure form. If vitamin lactones IV, contains hydroxy-protecting groups at C-3 and/or C-25, such groups may be removed by acid or base hydrolysis (depending on the protecting group present, as is well known in the art) to obtain the corresponding free hydroxy-lactone product VI where $R_1=R_2=H$.

Direct comparison with natural 25-hydroxyvitamin $D_3$-26,23-lactone shows that synthetic isomer VIC (where $R_1=R_2=H$) is identical with the natural product.

Alternatively the steroid lactone intermediate IV, as a mixture of its four stereoisomeric forms, may be subjected to photolysis by actinic irradiation as described above, to yield the corresponding mixture of the previtamin D lactone stereoisomers of general structure V. This mixture in turn is subjected to thermal isomerization as described above, to yield 25-hydroxyvitamin $D_3$-26,23-lactone, represented by general structure VI as a mixture of the four possible lactone stereo isomers. These stereo isomers can now be separated, preferably by HPLC, to yield in order of elution from the column, lactone stereo isomers, VIA, VIB, VIC, and CID, in pure form with isomer VIC corresponding to the natural product.

If desired, the synthetic process can also be conducted, by effecting an initial separation of the two C-23-hydroxy stereo-isomers of hydroxy-ketone 111 resulting from the aldol condensation step as described above by crystallization, or preferably, chromatography, to yield the two C-23-stereo-isomers in pure form (designated IIIA and IIIB for convenience here) and then subjecting each isomer separately to the subsequent steps of the described process (i.e. lactone formation, photolysis and thermal isomerization, steps 3, 4 and 5) to yield the desired vitamin lactone product of structure VI. In this manner, hydroxy-ketone isomer IIIA, subjected to the lactonization reaction (step 3) yields a mixture of lactone stereo-isomers IVB and IVD, which can be separated, preferably by HPLC, and separately converted by photolysis and thermal isomerization (steps 4 and 5) as described above to vitamin lactone products VIB and VID, respectively. Similarly, after the lactonization of the hydroxy-ketone isomer IIIB (step 3), a mixture of lactone isomers IVA and IVC is obtained, which, after separation, are converted by photolysis and isomerization (steps 4 and 5), to vitamin lactones VIA and VIC, respectively, where VIC, as mentioned above, corresponds to the natural product.

If desired, the steroid-lactone intermediate IV, shown in Process Schematic 1, can be obtained by an alternative but chemically analogous sequence, as depicted in Process Schematic 2.

PROCESS SCHEMATIC 2

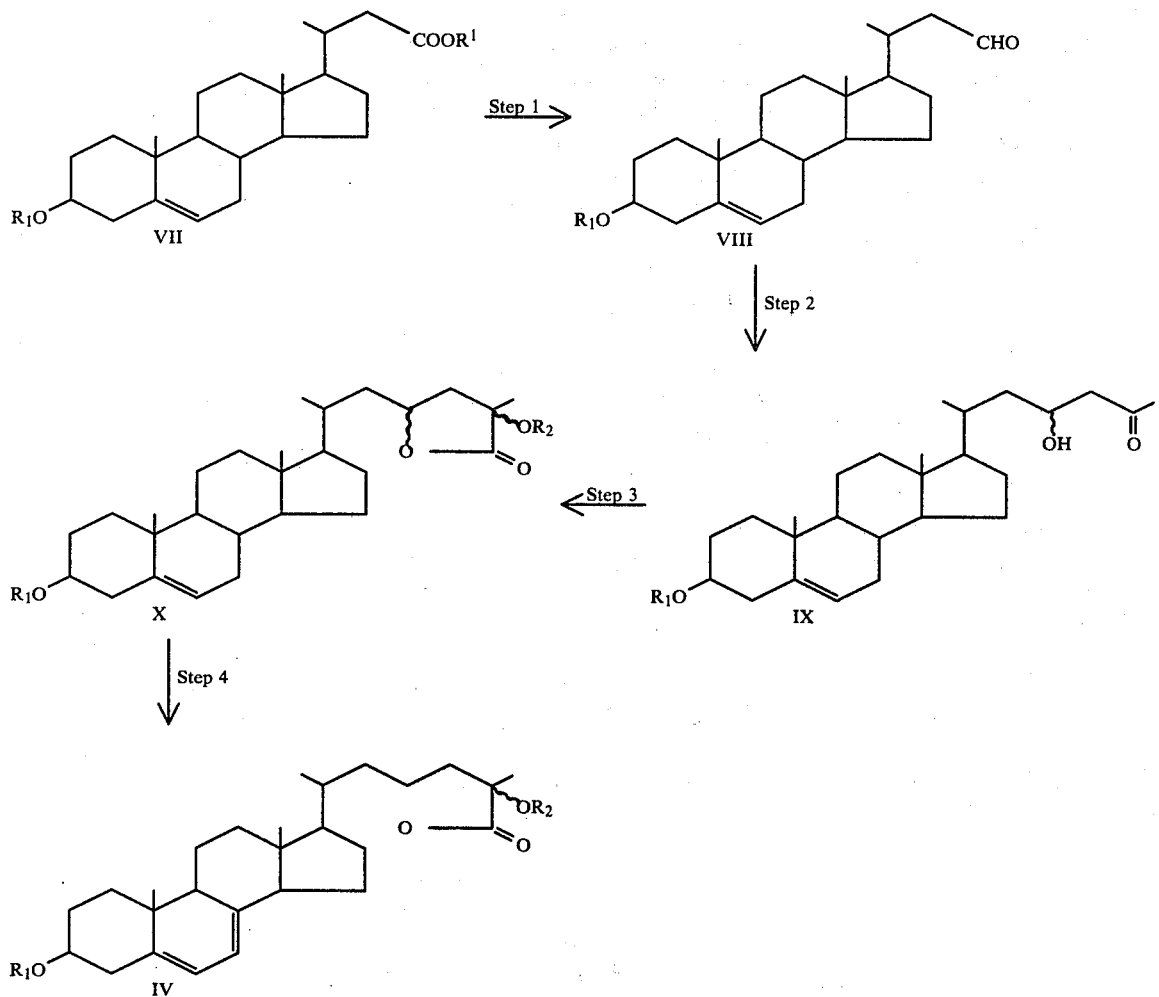

This process utilizes the known 24-nor-5-cholen-23-oic acid or its esters represented by structure VII (where $R_1$ and $R'$ designate substituents as defined for compound 1 in Process Schematic I), as starting material. Ester VII is reduced in step 1 to aldehyde VIII (where $R_1$ is hydrogen or a hydroxy protecting group) in a process entirely analogous to that discussed previously (i.e. step 1 of Process Schematic 1) and aldehyde VIII is subjected to an aldol condensation with acetone or an acetone equivalent to yield hydroxy-ketone IX, as a mixture of the two possible hydroxy stereo-isomers at carbon 23. Treatment of hydroxyketone IX (where $R_1$ is hydrogen or a hydroxy protecting group) with cyanide and subsequent hydrolysis using conditions analogous to those described above for step 3 of Process Schematic I yields the lactone intermediate X (where $R_1=R_2=H$) as a mixture of four possible (C-23 and C-25) stereo-isomeric forms. This product can then be converted to the corresponding 5,7-diene lactone IV described above, by well established methods, e.g. protection of the C-3-hydroxy group by acylation using standard conditions, followed by allylic bromination and dehydrobromination and removal of the C-3-acyl group by mild base hydrolysis. The four stereo-isomers of this product (compound IV) can now be separated, to yield in order of elution on the HPLC isomers IVA, IVB, IVC and IVD, as previously described. It is, of course, also possible to separate (preferably by HPLC) the two C-23-hydroxy stereo-isomers of hydroxy-ketone IX and to subject each epimer separately to the subsequent steps of the process (steps 3 and 4 of Process Schematic 2) in a manner entirely analogous to that described previously to obtain the same four stereo-isomers of lactone IV. Similarly, separation of the four lactone stereo-isomers can be effected at the stage of compound X (Process Schematic 2) and each of the lactone isomers XA, XB, XC and XD can then be separately converted to the corresponding 5,7-diene IVA, IVB, IVC and IVD, respectively, by the standard allylic bromination/dehydrobromination process.

Although in therapeutic applications of 25-hydroxyvitamin $D_3$ 26,23-lactone, the free hydroxy-lactone, represented by structure VI, where $R_1=R_2=H$, is normally the preferred form for administration, it is to be noted that a variety of derivatives of lactone VI, that may be desirable for certain applications can be readily prepared. Thus, acylation at moderate or low temperatures using acyl anhydride reagents and base catalysts provides the C-3-O-acyl derivatives of VI ($R_1$=acyl, $R_2$=H), whereas acylation at elevated temperatures (50°-70° C.) yields 3,25-di-O-acyl products (VI, $R_1=R_2$=acyl). For example, treatment of VI ($R_1=R_2=H$) which acetic anhydride and pyridine at 20° C. for 1–2 hours gives the corresponding 3-acetate derivative, whereas the 3,25-diacetate is readily formed when using the same reagents at 60° C. Similarly, alkylsilyl derivatives or tetrahydropyranyl derivatives of VI can be prepared by established procedures, and because of the differential reactivity of the C-3 and C-25-hydroxy groups, the 3-mono, or 3,25-di-protected derivatives are readily obtained. The 3-mono-acylated product, can be further derivatized at the C-25-hydroxy group, e.g. by acylation with a different acyl group or by alkylsilylation (with trimethylchlorosilane or similar reagents, or t-butyl-dimethylchlorosilane, etc) or tetrahydropyranylation according to procedures well known in the art.

Also in 3,25-di-protected derivatives of compound VI, the C-3-protecting group can be selectively removed by base or acid hydrolysis (depending on the protecting group present) to generate the 3-hydroxy-25-protected derivative (compound VI where $R_1=H$, $R_2=$hydroxy protecting group) and the 3-hydroxy group in such compounds may then be selectively derivatized with a group different from that present at C-25.

Alternatively and conveniently, free hydroxy groups in the steroid precursors to vitamin lactone VI can be protected and these hydroxy-protected derivatives can then be converted by the process steps detailed above to vitamin lactone VI, where $R_1$ or $R_2$, or both, represent hydroxy-protecting groups. Thus one or both of the hydroxy groups of 5,7-diene lactone IV ($R_1=R_2=H$ in Process Schematic I) or of $\Delta^5$-lactone X ($R_1=R_2=H$, in Process Schematic 2) can be derivatized by acylation, alkylsilylation, tetrahydropyranylation, etc.) exactly analogously to the procedures discussed earlier, to yield the corresponding mono- or di-hydroxy-protected derivatives (where the hydroxy protecting groups $R_1$ and $R_2$ can be the same or different). These derivatives can then be carried through the final process steps (e.g. steps 4 and 5 in Process Schematic I which are not affected by the nature of the hydroxy-protecting group present) to yield hydroxy-protected previtamin D lactone of structure V ($R_1$ or $R_2=$hydrogen or hydroxy protecting group) and then the desired mono- or di-hydroxy-protected vitamin D lactone of structure IV. It should be obvious also that these hydroxy-derivatization procedures can be applied to both mixtures of stereo-isomers (e.g. the mixtures of lactone isomers of compounds IV, X, VI or X) as well as the individual separated isomers (e.g. IV A, B, C, D, or VI A, B, C, D, etc.), although it is generally preferred to derivatize the individual stereo-isomers separately.

Other pharmaceutically useful derivatives of the lactone compounds described above can also be prepared. These are the corresponding hydroxy-carboxylic acids, resulting from lactone opening, i.e. compounds of the general structure XI

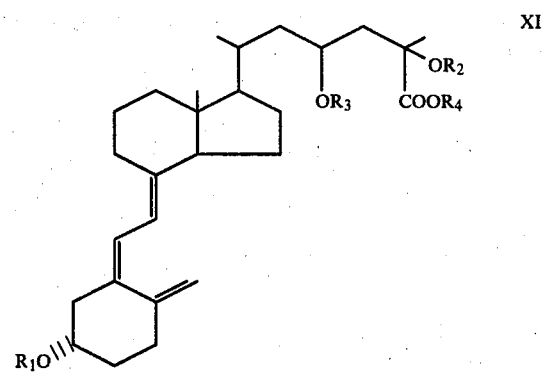

wherein each of $R_1$, $R_2$ and $R_3$ is hydrogen and where $R_4$ is hydrogen or a negative charge (i.e. carboxylate anion).

Such compounds are of particular interest because they are water-soluble derivatives of the described lactones. Because of their close structural relationship to the lactones they would be expected to possess intrinsic biological activity, or to express biological activity by virtue of their recyclization of the lactones in vivo (i.e. formation of compounds of type VI) since an equilibrium between lactone and hydroxy-carboxylic acid (or hydroxy carboxylate) must necessarily exist under in vivo conditions.

The hydroxy-acids of general structure XI are readily produced from lactones of general structure VI by hydrolysis of the lactone ring in base. Thus, treatment of the lactones VI in 0.01 to 0.1 M base (e.g. KOH or NaOH in $H_2O$ or $H_2O$/dioxane mixtures of $H_2O$/MeOH mixtures) at 25°–50° C. yields the corresponding ring-opened hydroxy-carboxylates, which, after careful acidification to pH 5–7, provide the hydroxy-carboxylic acids of structure IX (where $R_1$, $R_2$, $R_3$ and $R_4$ are hydrogen). The corresponding hydroxy-esters of structure XI, where $R_1$, $R_2$ and $R_3$ represent hydrogen and $R_4$ is an alkyl group can be produced in analogous fashion, by cleavage of the lactone in alcoholic base. For example, treatment of the lactones with sodium ethoxide in ethanol yields the ethyl ester of structure XI, wherein $R_1$, $R_2$ and $R_3$ are hydrogen and $R_4$ is ethyl. Other esters, e.g. the methyl propyl or butyl esters, can be prepared by analogous procedures utilizing the appropriate equivalent alcoholic base.

Additional derivatives of the hydroxy-esters such as may be desired for pharmaceutical preparations or other uses can be conveniently prepared by known methods. For example, using the derivatization procedures (acylation, alkylsilylation, etc. or combination of these procedures) discussed hereinbefore derivatives carrying acyl, alkylsilyl or tetrahydropyranyl groups (or any combination of these groups) on any or all of the C-3, 23 or 25 hydroxy groups (e.g. compounds of general structure XI wherein each of $R_1$, $R_2$ and $R_3$ is selected from hydrogen, acyl, alkylsilyl and tetrahydropyranyl, and where $R_4$ is alkyl) can be readily prepared.

It should be noted also that hydroxy-acids or hydroxy-esters of general structure XI, or their O-protected (acylated, alkylsilylated) derivatives can also be prepared from the corresponding steroid intermediates. For example, the base hydrolysis of the lactone ring of the 5,7-diene intermediate IV (Process Schematic I), utilizing a procedure analogous to that described above for lactone opening in the case of vitamin-lactone VI, yields the hydroxy-acid of the general structure

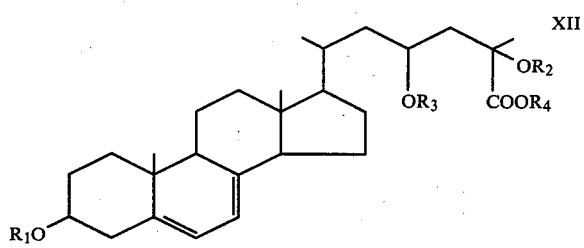

XII wherein $R_1$, $R_2$, $R_3$ and $R_4$ are hydrogen. Ultraviolet irradiation of this substance, as described for the analogous step in Process Schematic I, yields the corresponding pre-vitamin D-hydroxy-acid having structure XIII below.

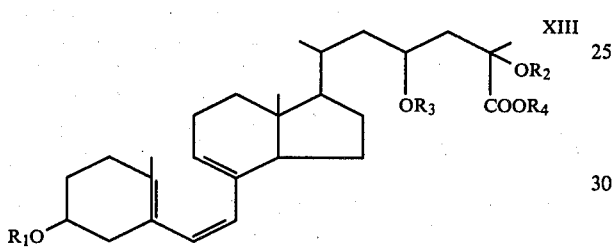

XIII

This pre-vitamin compound can be isomerized by heating in an inert solvent as described previously to give the vitamin hydroxy acid XI ($R_1$, $R_2$, $R_3$ and $R_4$=H). Similarly alcoholysis of the 5,7-dienelactone IV (e.g. NaOMe in MeOH; NaOEt in EtOH) yields the corresponding ester of structure XII (where $R_1$, $R_2$ and $R_3$=H and $R_4$=alkyl) from which hydroxy-ester hydroxy-protected derivatives (e.g. O-acyl, O-alkylsilyl, O-tetrahydropyranyl represented by structure XII, wherein each of $R_1$, $R_2$ and $R_3$ is selected from hydrogen, acyl, alkylsilyl, and tetrahydropyranyl and where $R_4$=alkyl) can be readily obtained by the derivatization procedures previously discussed. Ultraviolet irradiation of the hydroxy ester or its O-protected derivatives yields the previtamin D compounds of general structure XIII where each of $R_1$, $R_2$ and $R_3$ is selected from hydrogen, acyl, alkylsilyl and tetrahydropyranyl and where $R_4$ is alkyl. Subsequent thermal isomerization of these previtamin-intermediates yields the hydroxy esters of their corresponding O-protected derivatives of general structure VI, where each of $R_1$, $R_2$ and $R_3$ is selected from hydrogen, acyl, alkylsilyl and tetrahydropyranyl and where $R_4$ is alkyl.

If desired, the lactone opening reaction, using procedures entirely analogous to those described above can also be applied to the lactone steroid intermediate X (Process Schematic 2) to yield the corresponding hydroxy acids or hydroxy esters represented by general structure XIV below

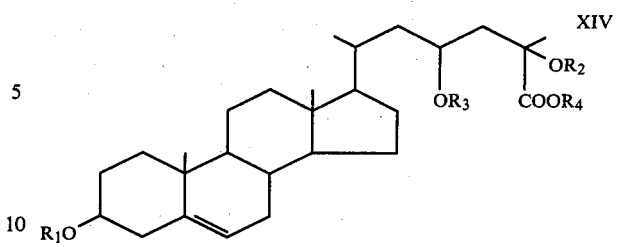

XIV where $R_1$, $R_2$ and $R_3$ are hydrogen and $R_4$ is hydrogen or alkyl. Such analogs, or their O-protected derivatives, can be readily converted to the corresponding vitamin hydroxy-acids or esters of structure XI, via dehydrogenation to compounds of general structure XII, subsequent photochemical conversion to intermediates of type XIII and thermal isomerization to the final products of structure XI using established and well known procedures.

EXAMPLE 1

To 269 mg of methyl 3β-hydroxy-24-norchola-5,7-dien-23-oate 3-acetate (compound 1, where $R_1$=acetyl and R'=methyl) in 12 ml toluene at −78° C. is added 0.72 ml of a 25% solution of lithium diisobutyl aluminum hydride in toluene. After 30 min, the solution is warmed to 4° C. and 4 ml of saturated $NH_4Cl$ is added and the mixture is stirred for 5 min. Water (25 ml) is then added and the reaction mixture is extracted with 100 ml $Et_2O$. The ether phase is separated and washed with 25 ml each of 1 N HCl, saturated $NaHCO_3$, saturated NaCl. The crude reaction mixture is applied to a 1×30 cm silica gel column and eluted with 6% EtOAc in hexane which elutes compound I and then with 16% and 22% EtOAc/hexane until the desired aldehyde product, compound II, is recovered (127.5 mg). The 23-aldehyde (compound II with $R_1$=H) exhibits the following spectral properties: U.V. absorption, $\lambda_{max}$=282, 272, 292 (shoulder); mass spectrum: m/e 342.2545 (calcd. 342.2558), 100%, M+; m/e 309, 65%, M+—$H_2O$—$CH_3$; m/e 283, 40%, M+—$2CH_3$—CHO; m/e 143, 50%, $C_{11}H_{11}$+; NMR: δ 9.77, s, 1H, C-23; 5.56, m, 1H, C-6; 5.40, m, 1H, C-7; 3.66, m, 1H, C-3; 1.05, d, J=6.2, 3H, C-21; 0.95, s, 3H, C-19; 0.67, s, 3H, C-18.

EXAMPLE 2

A mixture of 1.5 ml of acetone and 30 μl of 1.0 M KOH in methanol is prepared, and after 15 min at 0° C. is added to 122 mg compound II ($R_1$=H) dissolved in 0.5 ml acetone. The reaction mixture is stirred at 0° C. for 1.5 hr then 50 ml $H_2O$ is added and the mixture extracted 3× with 75 ml $CH_2Cl_2$. The crude reaction mixture is subjected to HPLC on a 0.79×30 cm silica gel column (μPorasil, a product of Waters Associates, Medford, Mass.) eluted with 2.25% isopropyl alcohol in $CH_2Cl_2$ at a flow rate of 3 ml/min. This procedure elutes 37.5 mg of starting material (compound II) at 12 ml followed by the desired hydroxy-ketone (C-23-stereo isomers (compound III, $R_1$=H) namely isomer IIIA (39.5 mg) eluting at 42 ml and isomer IIIB (37.3 mg) eluting at 46.5 ml. Spectral data for isomer IIIA: U.V. absorption spectrum $\mu_{max}$=282, 272, 292 (shoulder), mass spectrum, m/e 400.2983 (calcd. 400.2978) 100%, M+; 382, 22%, M+—$H_2O$; 367, 30%, M+—$H_2O$—$CH_3$; 342, 60%, M+—$C_3H_6O$; 309, 28%, M+—$C_3$-

$H_6O$—$CH_3$—$H_2O$; 271, 26%, $M^+$-side chain; 253, 12%, $M^+$-side chain-$H_2O$; NMR: δ 5.56, m, 1H, C-6; 5.39, m, 1H, C-7; 4.17, m, 1H, C-23; 3.63, m, 1H, C-3; 2.17, s, 3H, C-26; 0.99, d, J=6.2, 3H, C-21; 0.94, s, 3H, C-19; 0.65, s, 3H, C-18. For isomer IIIB: U.V. absorption spectrum, $\lambda_{max}$=282, 272, 292 (shoulder); mass spectrum: m/e 400.2983 (calcd. 400.2978) 100%, $M^+$; 382, 19%, $M^+$—$H_2O$; 367, 25%, $M^+$—$H_2O$—$CH_3$; 342, 93%, $M^+$—$C_3H_6O$; 309, 38%, $M^+$—$C_3H_6O$—$CH_3$—$H_2O$; 271, 28%, $M^+$-side chain; 253, 15%, $M^+$-side chain—$H_2O$; NMR: δ, 5.56, m, 1H, C-6; 5.40, m, 1H, C-7; 4.14, m, 1H, C-23; 3.64, m, 1H, C-3; 2.19, s, 3H, C-26; 1.00, d, J=5.5, 3H, C-21; 0.94, s, 3H, C-19; 0.63, s, 3H, C-18.

EXAMPLE 3

To a solution of 34 mg of hydroxy-ketone isomer IIIA ($R_1$=H) in 0.8 ml of EtOH at 50° C. is added 0.1 ml of a slurry of cyanide (prepared by grinding 340 mg NaCN and 540 mg $CaCl_3.2H_2O$ in a morter to homogeniety, and slurrying 45 mg of the resulting mixture in 1 ml of water), and after 5 and 10 min, additional 0.1 ml aliquots of the same slurry are added. After 1 hr, 0.15 ml of cyanide slurry is added together with 0.5 ml EtOH, and this addition is repeated at 2.5 hr. After 4.5 hr, 50 ml $H_2O$ is added and pH adjusted to ca. 1.5 with 1 N HCl. The reaction mixture is extracted with 4×50 ml $CH_2Cl_2$. The crude products, in 5 ml EtOH, are then treated with 1 ml 1 N HCl added at 45° C. for 1 hr. Water (25 ml) is then added and product is extracted with three 50 ml portions of $CH_2Cl_2$.

The crude product is subjected to HPLC on 2 Zorbax SIL semi-preparative columns (0.62×25 cm) in series eluted with 5% isopropanol in hexane at a flow rate of 3 ml/min to give lactone IV ($R_1$=H, $R_2$=H) as the expected two C-25-stereoisomers, designated IVB (4.3 mg) eluting at 90 ml, and IVD (4.0 mg) eluting at 129 ml. Spectral data for IVB ($R_1$=$R_2$=H), U.V. absorption spectrum, $\lambda_{max}$=282, 272, 292 (shoulder); mass spectrum: m/e 428.2935 (calcd. 428.2927), 100%, $M^+$; 410, 14%, $M^+$—$H_2O$; 395, 53%, $M^+$—$H_2O$—$CH_3$; 369, 22%, $M^+$—$C_3H_7O$; 271, 58%, $M^+$-side chain; 253, 28%, $M^+$-side chain—$H_2O$; 143, 63%, $C_{11}H_{11}^+$; NMR: δ 5.57, m, 1H, C-6; 5.40, m, 1H, C-7; 4.75, m, 1H, C-23; 3.64, m, 1H, C-3; 1.52, s, 3H, C-27; 1.04, d, J=5.9, 3H, C-21; 0.94, s, 3H, C-19; 0.64, s, 3H, C-18.

Spectral data for IVD: U.V. absorption spectrum, $\lambda_{max}$=282, 272, 292 (shoulder); mass spectrum: m/e 428.2927 (calcd. 428.2927), 100%, $M^+$; 410, 15%, $M^+$—$H_2O$; 395, 65%, $M^+$—$H_2O$—$CH_3$; 369, 30%, $M^+$—$C_3H_7O$; 271, 44%, $M^+$-side chain; 253, 25%, $M^+$-side chain—$H_2O$; 143, 90%, $C_{11}H_{11}^+$; NMR: δ 5.56, m, 1H, C-6; 5.40, m, 1H, C-7; 4.47, m, 1H, C-23; 3.63, m, 1H, C-3; 1.50, s, 3H, C-27; 1.03, d, J=6.6, 3H, C-21; 0.94, s, 3H, C-19; 0.65, s, 3H, C-18.

Hydroxy-ketone stereoisomer IIIB ($R_1$=H) subjected to the identical lactonization sequence also yields (from 29 mg of IIIB) two lactone stereoisomers, namely IVA ($R_1$=$R_2$=H) (2.9 mg) eluting at 80 ml in the HPLC system described above and lactone isomer IVC ($R_1$=$R_2$=H) (2.4 mg) eluting at 107 ml. Spectral data for IVA: U.V. absorption spectrum, $\lambda_{max}$=282, 272, 292 (shoulder); mass spectrum: m/e 428.2931 (calcd. 428.2927) 100%, $M^+$; 410, 18%, $M^+$—$H_2O$; 395, 62%, $M^+$—$H_2O$—$CH_3$; 369, 33%, $M^+$—$C_3H_7O$; 271, 26%, $M^+$-side chain; 253, 19%, $M^+$-side chain—$H_2O$; 143, 70%, $C_{11}H_{11}^+$. NMR: δ 5.57, m, 1H, C-6; 5.40, m, 1H, C-7; 4.72, m, 1H, C-23; 3.65, m, 1H, C-3; 1.51, s, 3H, C-27; 1.05, d, J=6.1, 3H, C-21; 0.95, s, 3H, C-19; 0.63, s, 3H, C-18.

Spectral data for IVC: U.V. absorption spectrum, $\lambda_{max}$=282, 272, 292 (shoulder); mass spectrum: m/e 428.2917 (calcd. 428.2927) 100%, $M^+$; 410, 16%, $M^+$—$H_2O$; 395, 68%, $M^+$—$H_2O$—$CH_3$; 369, 37%, $M^+$—$C_3H_7O$; 271, 16%, $M^+$-side chain; 253, 16%, $M^+$-side chain—$H_2O$; 143, 70%, $C_{11}H_{11}^+$. NMR: δ, 5.57, m, 1H, C-6; 5.40, m, 1H, C-7; 4.44, m, 1H, C-23; 3.64, m, 1H, C-3; 1.49, s, 3H, C-27; 1.04, d, J=6.7, 3H, C-21; 0.94, s, 3H, C-19; 0.63, s, 3H, C-18.

EXAMPLE 4

One mg each of the lactone isomers IVA, IVB, IVC and IVD as obtained in Example 3, are photolysed separately in 150 ml of 20% benzene in diethylether using a quartz immersion well and Hanovia 608A36 lamp with corex filter. After 15 min irradiation each reaction mixture is subjected to HPLC on a Zorbax-SIL semi-preparative column 0.62×25 cm using 2.25% 2-propanol in methylene chloride as solvent. From lactone isomer IVA there is obtained the desired previtamin lactone VA ($R_1$=$R_2$=H) eluting at 34.5 ml; from isomer IVB there is obtained previtamin lactone VB eluting at 34 ml; from isomer IVC, the previtamin lactone VC, eluting at 33 ml is obtained, and from lactone isomer IVD, the corresponding previtamin lactone VD, eluting at 33 ml is obtained.

EXAMPLE 5

Each of the previtamin lactones VA, VB, VC and VD are immediately isomerized to the desired vitamin lactone of structure VI in 1 ml EtOH at 70° C. for 2 hr. Each reaction mixture is then subjected to HPLC on a Zorbax SIL semi-preparative column (0.62×25 cm) using 6% 2-propanol in hexane as eluant. Vitamin lactone VIA ($R_1$=$R_2$=H) (500 μg) is collected at 29.5 ml; vitamin lactone isomer VIB (500 μg) is collected at 31.5 ml; vitamin lactone isomer VIC (500 μg) is collected at 39.75 ml, and 500 μg of isomer VID is collected at 45.0 ml.

Spectral Data: VIA, mass spectrum, m/e 428.2923 (calcd. 428.2927) 24%, $M^+$; 410, 3%, $M^+$—$H_2O$; 395, 11%, $M^+$—$H_2O$—$CH_3$; 271, 2%, $M^+$-side chain; 253, 9%, $M^+$-side chain—$H_2O$; 136, 100%, A ring+$C_6$+$C_7^+$; 118, 82%, A ring+$C_6$+$C_7$—$H_2O$; NMR: δ 6.28, d, J=11.8, 1H, C-6; 6.03, d, J=11.0, 1H, C-7; 5.05, m(sharp), 1H, C-19(E); 4.82, m (sharp), 1H, C-19(Z); 4.72, m, 1H, C-23; 3.96, m, 1H, C-3; 1.51, s, 3H, C-27; 1.03, d, J=5.5, 3H, C-21; 0.56, s, 3H, C-18; Fourier transform infrared spectrum (FT-IR); 1780 $cm^{-1}$ (lactone C=O); UV: $\lambda_{max}$=265 nm, $\lambda_{min}$=228 nm.

VIB; mass spectrum, m/e 428.2927 (calcd. 428,2927), 27%, $M^+$; 410, 2%, $M^+$—$H_2O$; 395, 11%, $M^+$—$H_2O$—$CH_3$; 271, 2%, $M^+$-side chain; 253, 7%, $M^+$-side chain—$H_2O$; 136, 100%, A ring+$C_6$+$C_7^+$; 118, 92%, A ring+$C_6$+$C_7^+$—$H_2O$; NMR: δ 6.28, d, J=11.7, 1H, C-6; 6.03, d, J=11.1, 1H, C-7; 5.05, m (sharp), 1H, C-19(E); 4.82, m(sharp), 1H, C-19(Z); 4.75, m, 1H, C-23; 3.96, m, 1H, C-3; 1.52, s, 3H, C-27; 1.03, d, J=5.6, 3H, C-21; 0.56, S, 3H, C-18; FT-IR: 1781 $cm^{-1}$(lactone C=O); UV: $\lambda_{max}$=265 nm, $\lambda_{min}$=228 nm.

VIC; mass spectrum, m/e 428.2919 (calcd. 428.2927), 25%, $M^+$; 410, 2%, $M^+$—$H_2O$; 395, 9%, $M^+$—$H_2O$—$CH_3$; 271, 1%, $M^+$-side chain; 253, 8%, $M^+$-side chain—$H_2O$; 136, 100%, A ring+$C_6$+$C_7^+$; 118, 83%, A ring+$C_6$+$C_7^+$—$H_2O$; NMR: δ 6.28, d, J=11.8, 1H, C-6; 6.03, d, J=10.7, 1H, C-7; 5.05, m (sharp), 1H, C-

19(E); 4.82, m (sharp), 1H, C-19(Z); 4.44, m, 1H, C-23; 3.96, m, 1H, C-3; 1.49, s, 3H, C-27; 1.03, d, J=5.2, 3H, C-21; 0.56, s, 3H, C-18; FT-IR: 1784 cm$^{-1}$ (lactone C=O); UV: $\lambda_{max}$=265 nm, $\lambda_{min}$=228 nm.

VID: mass spectrum, m/e 428.2927 (calcd. 428.2927), 26%, M$^+$; 410, 1%, M$^+$—H$_2$O; 395, 11%, M$^+$—H$_2$O—CH$_3$; 271, 2%, M$^+$-side chain; 253, 7%, M$^+$-side chain—H$_2$O; 136, 100%, A ring+C$_6$+C$_7$$^+$; 118, 86%, A ring+C$_6$+C$_7$$^+$—H$_2$O; NMR: δ 6.28, d, J=11.8, 1H C-6; 6.03, d, J=11.0, 1H, C-7; 5.05, m (sharp), 1H, C-19(E); 4.82 m (sharp), C-19(Z); 4.47 m, 1H, C-23; 3.96, m, 1H, C-3; 1.50, S, 3H, C-27; 1.03, d, J=5.5, 3H, C-21, 0.56, s, 3H, C-18; FT-IR: 1784 cm$^{-1}$ (lactone C=O); UV: $\lambda_{max}$=265 nm, $\lambda_{min}$=285 nm.

EXAMPLE 6

Methyl 24-nor-5-cholen-23-oate (0.7 g) is reacted with 2 ml dihydropyran and 0.2 ml phosphorusoxychloride in 15 ml CH$_2$Cl$_2$ at room temperature for 40 min; 50 ml Et$_2$O is added and the mixture extracted with 2×25 ml saturated NaHCO$_3$ and 1×25 ml saturated NaCl. The Et$_2$O phase is evaporated to yield the crude tetrahydropyranyl derivative (compound VII of Process Schematice 2, where R$_1$=tetrahydropyranyl (THP) and R'=Me).

To a slurry of 0.3 g LAH in 15 ml Et$_2$O is added crude VII dissolved in 15 ml Et$_2$O at −78° C. At 30 min after final addition, the reaction is warmed to 0° C. and 10% NaOH in H$_2$O is slowly added with stirring until all flocculant material is white. The mixture is extracted with 100 ml Et$_2$O vs 3×50 ml H$_2$O, dried with MgSO$_4$ and concentrated to yield crude 23-alcohol.

To a solution of 12 molar excess pyridine in 30 ml CH$_2$Cl$_2$ on ice is added a 6 molar excess of CrO$_3$. The mixture is stirred for 30 min at which time crude 23-alcohol obtained as above in 20 ml CH$_2$Cl$_2$ is added. At 15 min the reaction is extracted 3×25 ml 50% NaHCO$_3$, dried with MgSO$_4$ and applied to a 2×36 cm silica column eluted with 5% EtOAc/hexane to recover 0.63 g of 23-aldehyde, represented by structure VIII of Process Schematic 2 where R$_1$=THP (78.6% yield from VII). Mass spectrum: m/e 428, 0.5%, M$^+$; 326, 80%, M$^+$-HOTHP; 298, 22%, M$^+$-HOTHP-CO; 85, 100%, C$_5$H$_9$O$^+$.

EXAMPLE 7 n-Butyl lithium (0.672 mmol) is slowly added to a solution of 0.672 mmol of diisopropyl amine in 5 ml Et$_2$O at −78° C.; 20 min after addition, 0.672 mmol of acetonecyclohexylimine is added and after 15 min, 250 mg of aldehyde VIII (R$_1$=THP) is slowly added in 10 ml Et$_2$O. After 30 min, the reaction is warmed to 0° C. and 10 ml H$_2$O is added and the mixture is stirred for 10 min. An additional 30 ml H$_2$O is then added and the mixture is extracted 3 times with 30 ml of diethyl ether. The ether phase is dried with MgSO$_4$ and applied to four 20×20 cm×750 μm silica TLC plates eluted with 25% EtOAc/hexane to give 60 mg of hydroxyketone IX (R$_1$=THP) (21% yield from VIII) as the two possible C-23-hydroxy stereoisomers. Mass spectrum: m/e, 486, 0.5%, M$^+$; 384, 35%, M$^+$-HOTHP; 366, 21%, M$^+$—HOTHP—H$_2$O; 326, 68%, M$^+$—HOTHP—C$_3$H$_6$O; 85, 100%, C$_5$H$_9$O$^+$.

EXAMPLE 8

To a solution of 37 mg IX (R$_1$+THP) in 1 ml EtOH is added 0.250 ml of acetonecyanohydrin. The mixture is reacted at room temperature for 12 hr at which time 0.32 g of KOH is added in 4 ml 1:1 H$_2$O-EtOH. The temperature is raised to 50° C. for 1 hr and enough 6 N HCl is then slowly added to bring the pH to ca. 1.0. The resulting mixture is stirred for 30 min at room temperature, then 30 ml H$_2$O is added and extracted 3 times with 30 ml of CH$_2$Cl$_2$. The CH$_2$Cl$_2$ phase is evaporated to yield after preliminary purification 18.6 mg of lactone X (R$_1$=H), representing a mixture of the four possible C-23 and C-25 stereoisomers (yield 57% from 5); mass spectrum: m/e 430, 88%, M$^+$; 412, 100%, M$^+$-H$_2$O; 397, 47%, M$^+$—H$_2$O—CH$_3$; 345, 30%, 319, 45%, 213, 93%. The four lactone stereoisomers can be separated by HPLC chromatography on silica gel (semi-preparative Zorbax-Sil column 0.62×25 cm) using 4.5% 2-propanol in hexane as eluting solvent.

Lactone X can be converted to 7-dehydrolactone IV by established procedures. Thus acetylation of X as obtained above with pyridine acetic anhydride yields the corresponding acetate which is subjected to allylic bromination (following well-known conditions dibromodimethylhydantoin) and then dehydrobrominated with trimethyl phosphite or collidine to yield the 5,7-diene lactone IV (R=acetyl) as a mixture of C-23 and C-25 epimers. These four epimers are separated as described in Example 3 to yield each stereoisomer, i.e. IVA, IVB, IVC and IVD in pure form.

As is evident from the foregoing specification, the structural formulas

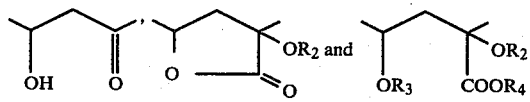

wherever they appear therein or in the appended claims are indicative of all their isomeric forms.

Having thus described the invention what is claimed is:

1. A process for preparing 25-hydroxyvitamin D$_3$-26,23-lactone, which comprises subjecting 3β,23-dihydroxy-26-norcholesta-5,7-diene-25-one to treatment with an inorganic cyanide or organic cyanohydrin under basic conditions in an alcoholic solvent, followed by treatment with a mineral acid, to obtain 3β,25-hydroxy-cholesta-5,7-diene-26,23-lactone, subjecting said lactone to actinic irradiation to obtain 25-hydroxy-previtamin D$_3$-26,23-lactone, and isomerizing said product by heating and recovering the desired 25-hydroxyvitamin D$_3$-26,23-lactone product.

2. Compounds having the formula

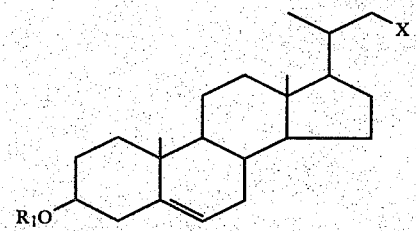

where X is selected from

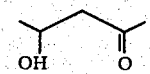

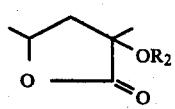

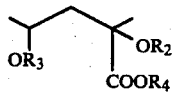

$R_1$, $R_2$ and $R_3$ are selected from the group consisting of hydrogen, acyl, alkylsilyl and tetrahydropryanyl and $R_4$ is hydrogen or alkyl in all their isomeric forms.

3. Compounds according to claim 2 wherein X is

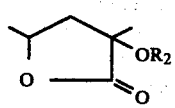

and each of $R_1$ and $R_2$, which may be the same or different, is selected from the group consisting of hydrogen, acyl, alkylsilyl and tetrahydropyranyl in all their isomeric forms.

4. Compounds according to claim 2 where X is

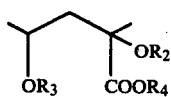

$R_1$, $R_2$ and $R_3$ are hydrogen, and $R_4$ is hydrogen or alkyl.

5. The compounds of claim 2 wherein X is

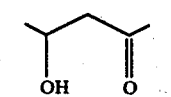

and $R_1$ is selected from hydrogen, acyl, alkylsilyl and tetrahydropyranyl.

6. Compounds having the formula

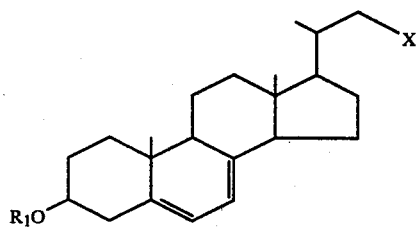

where X is selected from

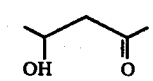

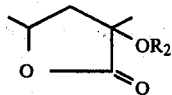

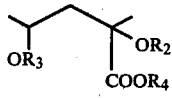

$R_1$, $R_2$ and $R_3$ are selected from the group consisting of hydrogen, acyl, alkylsilyl and tetrahydropyranyl and $R_4$ is hydrogen or alkyl in all their isomeric forms.

7. Compounds according to claim 6 wherein X is

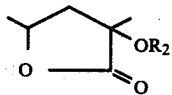

and each of $R_1$ and $R_2$, which may be the same or different, is selected from the group consisting of hydrogen, acyl, alkylsilyl and tetrahydropyranyl in all their isomeric forms.

8. Compounds according to claim 6 wherein X is

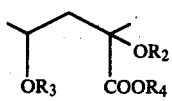

and $R_1$, $R_2$, $R_3$ and $R_4$ are hydrogen.

9. The compounds of claim 6 wherein X is

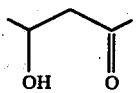

and $R_1$ is selected from hydrogen, acyl, alkylsilyl and tetrahydropyranyl.

10. Compounds having the formula

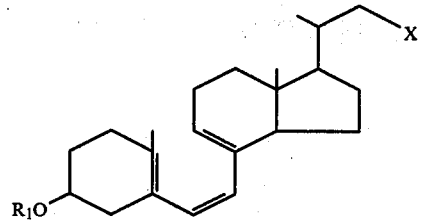

where X is selected from

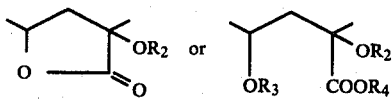

$R_1$, $R_2$ and $R_3$ are selected from the group consisting of hydrogen, acyl, alkylsilyl and tetrahydropyranyl and $R_4$ is hydrogen or alkyl in all their isomeric forms.

11. Compounds according to claim 10 wherein X is

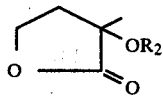

and each of $R_1$ and $R_2$, which may be the same or different, is selected from the group consisting of hydrogen, acyl, alkylsilyl and tetrahydropyranyl in all their isomeric forms.

12. Compounds according to claim 10 wherein X is

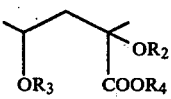

$R_1$, $R_2$ and $R_3$ are hydrogen and $R_4$ is hydrogen or alkyl.

13. The compounds having the formula

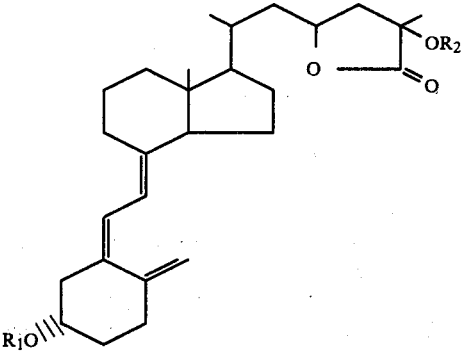

wherein each of $R_1$ and $R_2$, which may be the same or different, is selected from the group consisting of hydrogen, acyl, alkylsilyl and tetrahydropyranyl, except that, when the stereochemical configuration at carbon-23 and 25 is as it occurs in 25-hydroxyvitamin $D_3$-26,23-lactone derived from natural sources, $R_1$ and $R_2$ may not both be hydrogen.

14. Compounds having the formula

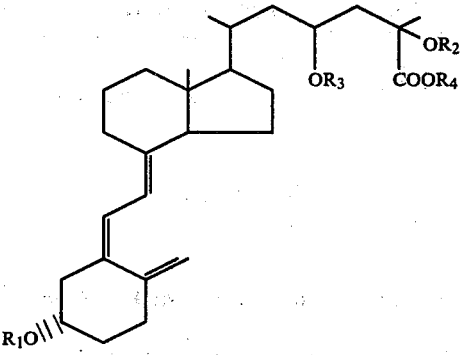

where $R_1$, $R_2$ and $R_3$ are selected from the group consisting of hydrogen, acyl, alkylsilyl and tetrahydropyranyl and $R_4$ is hydrogen or alkyl.

15. The compounds of claim 14 wherein $R_1$, $R_2$, $R_3$ and $R_4$ are hydrogen.

16. The compounds of claim 14 wherein $R_1$, $R_2$ and $R_3$ are hydrogen and $R_4$ is alkyl.

* * * * *

UNITED STATES PATENT OFFICE
CERTIFICATE OF CORRECTION

Patent No. 4,336,193            Dated June 22, 1982

Inventor(s) Hector F. DeLuca et al

It is certified that error appears in the above-identified patent and that said Letters Patent are hereby corrected as shown below:

In Column 5, at line 35, the structural formula,

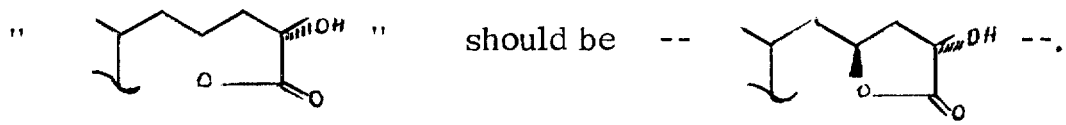

In Column 7, at PROCESS SCHEMATIC 2,

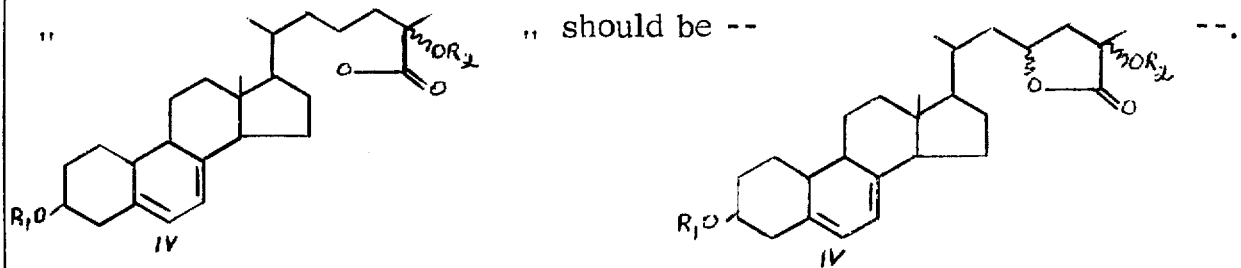

Signed and Sealed this

Twenty-fourth Day of August 1982

[SEAL]

Attest:

GERALD J. MOSSINGHOFF

Attesting Officer        Commissioner of Patents and Trademarks